(12) United States Patent
Soers et al.

(10) Patent No.: US 9,719,969 B2
(45) Date of Patent: *Aug. 1, 2017

(54) ANALYSIS OF MOLECULAR CONTAMINATION IN VACUUM ENVIRONMENTS

(71) Applicant: KONINKLIJKE PHILIPS N.V., Eindhoven (NL)

(72) Inventors: Ruud Johannes Theodorus Soers, Budel (NL); Hugo Hubertus Knobel, Eindhoven (NL); Pieter Klaas De Bokx, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 15 days.

This patent is subject to a terminal disclaimer.

(21) Appl. No.: 15/164,278

(22) Filed: May 25, 2016

(65) Prior Publication Data

US 2016/0266075 A1    Sep. 15, 2016

Related U.S. Application Data

(63) Continuation of application No. 13/876,200, filed as application No. PCT/IB2011/054678 on Oct. 25, 2010, now Pat. No. 9,375,671.

(30) Foreign Application Priority Data

Oct. 25, 2010  (EP) .................................... 10188653

(51) Int. Cl.
*G01N 30/08* (2006.01)
*G01N 1/40* (2006.01)
(Continued)

(52) U.S. Cl.
CPC ........... *G01N 30/08* (2013.01); *B01D 53/025* (2013.01); *B01D 53/0407* (2013.01);
(Continued)

(58) Field of Classification Search
CPC ........................... B01D 53/0407; G01N 1/405
See application file for complete search history.

(56) References Cited

U.S. PATENT DOCUMENTS 4,049,395 A    9/1977 Ito
4,059,657 A    11/1977 Hay
(Continued)

FOREIGN PATENT DOCUMENTS

JP    04177161 A    6/1992
JP    10197503 A    7/1998
(Continued)

OTHER PUBLICATIONS

Han et al, "Continuous Preconcentrator for Trace Gas Analysis", Recent Patents on Mechanical Engineering, 2009, vol. 2, pp. 214-227.

*Primary Examiner* — Laura Martin
*Assistant Examiner* — Alex Devito

(57) ABSTRACT

A pre-concentration device is provided for a gas analysis system (10) for collecting molecular contamination in a vacuum environment (11). The pre-concentration device (13) comprises a hollow element (15) having an entrance opening (20) for receiving molecules from the vacuum environment (11) in a collection phase, a gas outlet for transferring collected molecules to a vacuum compatible detector or second preconcentration device in a transfer phase. The device has an inner wall for adsorbing molecules in the collection phase and desorbing molecules in the transfer phase. The device has a filler element (14) that is movable from a first position outside the hollow element in
(Continued)

the collection phase to a second position inside the hollow element in the transfer phase which second position leaves open a transfer channel to the gas outlet along the inner wall. Advantageously, the device enables transferring of the organic or inorganic contaminants collected in the device under vacuum conditions, and requires a minimal amount of ultra pure gas for the transport of the contaminants to a detector or further a concentration device, which lowers the lower limit of detection.

10 Claims, 4 Drawing Sheets

(51) Int. Cl.
| | | |
|---|---|---|
| G01N 33/00 | (2006.01) | |
| B01D 53/04 | (2006.01) | |
| G01N 30/06 | (2006.01) | |
| B01D 53/02 | (2006.01) | |
| G01N 30/72 | (2006.01) | |
| G01N 30/02 | (2006.01) | |

(52) U.S. Cl.
CPC .............. *G01N 1/405* (2013.01); *G01N 30/06* (2013.01); *G01N 30/7206* (2013.01); *G01N 33/0011* (2013.01); *G01N 2030/025* (2013.01); *G01N 2033/0019* (2013.01)

(56) References Cited

U.S. PATENT DOCUMENTS

| | | |
|---|---|---|
| 4,500,432 A | 2/1985 | Poole et al. |
| 5,055,696 A | 10/1991 | Haraichi et al. |
| 5,288,310 A | 2/1994 | Peters et al. |
| 5,313,858 A | 5/1994 | Stitt |
| 5,481,110 A | 1/1996 | Krishnaswamy et al. |
| 6,055,845 A | 5/2000 | Gerstel et al. |
| 7,621,171 B2 | 11/2009 | O'Brien |
| 7,799,279 B2 | 9/2010 | Fulton et al. |
| 2008/0148815 A1 | 6/2008 | Lucas et al. |
| 2009/0090197 A1 | 4/2009 | Finlay et al. |

FOREIGN PATENT DOCUMENTS

| | | |
|---|---|---|
| JP | 2008235416 A | 10/2008 |
| JP | 201003701 A | 2/2010 |
| WO | 2011007280 A2 | 1/2011 |

ANALYSIS OF MOLECULAR CONTAMINATION IN VACUUM ENVIRONMENTS

CROSS-REFERENCE TO PRIOR APPLICATIONS

This application claims the benefit or priority of and describes relationships between the following applications: wherein this application is a continuation of U.S. patent application Ser. No. 13/876,200, filed Mar. 27, 2013, which is the National Stage of International Application No. PCT/IB2011/054678, filed Oct. 20, 2011, which claims the priority of foreign application EP10188653.9 filed Oct. 25, 2010, all of which are incorporated herein in whole by reference.

FIELD OF THE INVENTION

The invention relates to a pre-concentration device for a gas analysis system for detecting molecular contamination in a vacuum environment, the pre-concentration device comprising a hollow element having a gas entrance opening for receiving gas from the vacuum environment in a collection phase, a gas outlet for transferring gas to a vacuum compatible detector or a second pre-concentration device in a transfer phase, and an inner wall for adsorbing gas in the collection phase and desorbing gas in the transfer phase.

The invention further relates to a gas analysis system for detecting molecular contamination in a vacuum environment, the system comprising the pre-concentration device and a pump system for transporting gas via the hollow element to the gas outlet.

This invention further relates to a method of pre-concentration in a gas analysis system for detecting molecular contamination in a vacuum environment, and a method of analyzing gas for detecting molecular contamination in a vacuum environment.

BACKGROUND OF THE INVENTION

The control of molecular contamination in advanced semiconductor processing is critical to successful manufacturing. The use of very short wavelengths (Extreme Ultraviolet, EUV; 13.5 nm) increases photo-chemical decomposition and subsequent deposition of contaminants on optical parts. The results are yield loss, shortened tool life and reduced long-term device reliability. Therefore, very strict specifications on the out-gassing of organics are imposed on sub-assemblies and parts used in semiconductor manufacturing equipment.

The document US2009/0090197 describes pre-concentrator devices for use in a gas analysis or detector system. Various detachable pre-concentrators may be used in a cascade. The document describes pre-concentration and detection in atmospheric pressure.

In vacuum or low pressure circumstances, it is difficult to pump a sufficient amount of gas through a detection system. In such circumstances it is known to use a pre-concentration device. In a pre-concentration device, the molecular contamination is gathered during a relatively long time span, called a collection phase now. Then, the gathered molecules are released in a relatively short time interval, called a transfer phase now. From an analysis of the released gas, the molecular contamination can be determined.

An example of a known pre-concentration device is shown in FIG. 2. The pre-concentration device is a hollow tube packed with sorbent material. The interconnecting open spaces between the particles in the packed bed can be thought of as a large number of capillaries with a much smaller effective diameter than the device they are packed into. Reduced effective diameter leads to reduced gas flow. In normal circumstances that would not be a problem. However, when working in the molecular or transition flow range (vacuum or very low pressure), a reduced effective diameter may cause bigger problems. Because the conductivity of the device and the gas flow in the molecular and transition flow range are highly dependent on the cross sectional area of the device it must flow through, the gas flow decreases drastically. The inset shows the particles of the sorbent and the path which interconnecting open spaces between the particles in the packed bed can be thought of as a large number of capillaries with a much smaller effective diameter than the device they are packed into. When working in the molecular or transition flow range, the above described pre-concentration device thus has a serious problem with the gas flow, which results in extraordinary long sampling times (e.g. months) when low detections limits are required (e.g. ppbV, pptV).

SUMMARY OF THE INVENTION

It is an object of the invention to provide a pre-concentration device for a gas analysis system according to the opening paragraph, which system is capable of effectively pre-concentrating gas and determining molecular contamination in a vacuum or low pressure environment.

According to a first aspect of the invention, this object is achieved by providing a pre-concentration device for a gas analysis system as defined in the opening paragraph, the pre-concentration device further comprising a filler element that is movable from a first position outside the hollow element in the collection phase to a second position inside the hollow element in the transfer phase which second position leaves open a transfer channel to the gas outlet along the inner wall.

According to a further aspect of the invention, the object is achieved by a method of pre-concentration as defined in the opening paragraph, the system comprising the above pre-concentration device, the method comprising positioning the filler element in the first position outside the hollow element in a collection phase, receiving gas via the gas entrance opening from the vacuum environment and adsorbing the gas species of interest on the inner wall in the collection phase, moving the filler element to the second position inside the hollow element in the transfer phase which second position leaves open a transfer channel to the gas outlet along the inner wall, and desorbing gas in the transfer phase from the inner wall and transferring the gas via the gas outlet to a vacuum compatible detector or a second pre-concentration device in the transfer phase.

The measures have the effect that, during the collection phase, a large effective area is available for adsorbing the gas. The large effective area is achieved by the surface of the entrance opening and the inner wall of the pre-concentration device bounding the space beyond the entrance opening, i.e. the inner space of the pre-concentration device. Subsequently, after the collection phase, the filler element is moved to the second position, which is inside the inner space of the pre-concentration device. Hence the volume of the inner space is effectively reduced, and the remaining space now constitutes a low volume transfer channel towards the gas outlet. Subsequently, during the transfer phase, the gas outlet is opened and gas is desorbed from the inner wall, i.e.

released in said remaining volume. Advantageously, due to the filler element, the device provides an increased gas concentration in the transfer channel, and the concentrated gas is transported via gas outlet, e.g. to a further concentration unit or a detector unit. The system may be used for detecting any type of molecules present in the vacuum environment, e.g. molecular organic or inorganic contamination.

Optionally, the outer wall of the filler element may also be arranged for adsorbing gas in the collection phase, and releasing the gas in the transfer phase.

The invention is also based on the following recognition. The effectiveness of the gas analysis system according to the invention comes from a combination of two important new features. To maximize the conductivity of the system and to maintain a sufficient gas flux from the reduced pressure/vacuum system through the pre-concentration device, obstructions forming a limited access to an adsorbing surface are reduced by providing a relatively large entrance opening which allows gas molecules to travel towards the adsorbing surface. The increased conductivity of the device enables sufficient transport of gas molecules from the reduced pressure/vacuum environment to the inner wall of the pre-concentration device. Moreover, the effectively large entrance opening towards the inner wall of the hollow element in the collection phase is followed by reducing the effective opening and inner volume of the device in the transfer phase. Gas is released from the inner wall by desorbing in the reduced inner volume and will be more concentrated. Also, due to the reduced opening, only few molecules will travel backwards to the vacuum environment, while the majority will travel towards the gas outlet. The flux is achieved by pumping the gas through a vacuum compatible detector or second pre-concentration device.

Optionally, the device comprises a flow inlet for admitting a purge medium for enabling transporting of the desorbed gas or rinsing of the pre-concentration device. The purge medium, e.g. an ultrapure gas, may be guided towards the vacuum environment, or to a starting point of the transfer channel.

Optionally, the hollow element has an inner space bounded by the inner wall, and the inner space has a conical shape, and the filler element has a shape corresponding to the conical shape of the inner space such that, in the second position, the transfer channel is formed between the filler element and the inner wall. Advantageously the conical shape of both the inner space and the filler element enables, in the second position, forming a suitable, narrow transfer channel between the inner wall and the outer wall of the filler element.

Optionally, the device comprises a closing element for closing the gas entrance opening in the transfer phase. The closing element may be shaped to fully or at least substantially closing the entrance opening in the transfer phase. In particular, the filler element may be shaped to comprise the closing element for at least substantially reducing the gas entrance opening. In practice, the closing element may be a flange on the filler element. Also, the closing element may be further arranged for, in the transfer phase, reducing the gas entrance opening to a reduced inlet for admitting gas from the vacuum environment for transporting the desorbed gas to the gas outlet. Advantageously the reduced inlet allows gas from the vacuum environment to enter the transfer channel, e.g. remaining gas and/or a transport gas intentionally admitted to the vacuum environment.

Optionally, the inner wall or the filler element comprises a coating of adsorbent particles. Applying adsorbent particles to the inner wall of the pre-concentration device and/or the filler element may result in a further improvement of the gas analysis system. The type of particles may be chosen to enhance the collection of specific gas molecules, thereby enhancing the amount of the specific gas molecules, i.e. effectively lowering the detection limit.

Optionally, the device is arranged for coupling to a cooling means for cooling of the inner wall or the filler element in the collection phase and/or for coupling to a heating means for heating of the inner wall or the filler element in the transfer phase. At room temperature many molecules that should be collected by the concentration device would enter and leave the pre concentration device without adsorbing for a sufficient amount of time. Therefore, the gas analysis system according to the invention further may comprise cooling means for cooling of the inner wall or the filler element in the collection phase. The cooling means cause the molecules colliding with the inner wall of the hollow element or the filler element to lose adsorption heat and thereby increasing the residence time of molecules adsorbed on the inner wall. For example, the pre-concentration device may comprise a coolant inlet being coupled to the cooling means and the cooling means is arranged for providing a coolant to the pre-concentration device. For example, liquid nitrogen may be sent through cooling channels in the hollow element in order to cool the pre-concentration device from within. Alternatively, the pre-concentration device as a whole may be cooled from the outside of the hollow element. Furthermore, heating means may be provided and coupled to the pre-concentration device in the transfer phase. Releasing the adsorbed molecules from the inner wall or the filler element, also called desorbing, will be enhanced and speeded up by heating.

Optionally, the device may comprise a flow inlet for admitting a purge medium for enabling transporting of the desorbed gas or rinsing of the pre-concentration device. The inlet may be a purge flow inlet for enabling rinsing of the pre-concentration device. Admitting a preferably pure gas to a starting point of the transfer channel is important for the transport of substantially all collected contaminants to the analysis system after desorption, and/or for cleaning the pre-concentration device before re-using it for a further measurement.

A gas analysis system comprising the above pre-concentration device may further comprise a pump system for transporting, via the pre-concentration device, gas to be adsorbed from the vacuum environment to the inner wall, or gas desorbed from the inner wall via the transfer channel to the gas outlet. The pump system may decrease the pressure in the transfer phase via the gas outlet. The gas analysis system may comprise gas insertion means for inserting an amount of a known gas into the vacuum environment in order to promote the transport of gas molecules by the pumping system. In a vacuum, it may be very difficult to transport the few contaminating molecules through the transfer channel of the pre-concentration device, towards a second pre-concentration device or vacuum compatible detector. If, before or during the pumping in the transfer phase, a small amount of known gas is brought into the vacuum environment, the transport will be improved and the chance of all contaminating molecules being transferred increases. The 'known gas' preferably is an ultra pure gas, but may be a gas mixture with a predetermined composition.

Optionally, the gas analysis system may comprise a cooling means for cooling the inner wall or the filler element in the collection phase, and/or a heating means for heating the inner wall or the filler element in the transfer phase, and/or a vacuum compatible detector for quantitative and qualitative analysis of the collected molecules released. Optionally, the method of analyzing gas comprises a step of gas chromatography for analysis of the released gas for determining the molecular contamination, and/or a step of mass spectrometry and/or a step of element specific detection for analysis of the released gas for determining the molecular contamination.

These and other aspects of the invention are apparent from and will be elucidated with reference to the embodiments described hereinafter. Further preferred embodiments of the device and method according to the invention are given in the appended claims, disclosure of which is incorporated herein by reference.

BRIEF DESCRIPTION OF THE DRAWINGS

In the drawings.

The figures are purely diagrammatic and not drawn to scale. In the Figures, elements which correspond to elements already described have the same reference numerals.

DETAILED DESCRIPTION OF EMBODIMENTS

Figure 1:
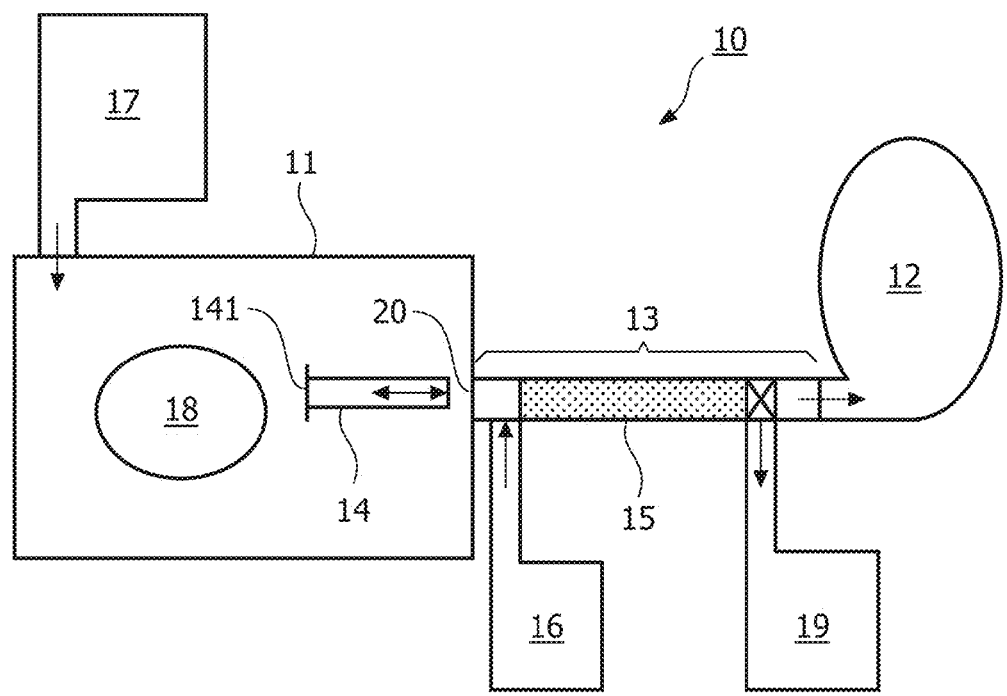
FIG. 1 schematically shows a gas analysis system according to the invention.

FIG. 1 schematically shows a gas analysis system 10 according to the invention. The system 10 is used for detecting molecules which are out-gassed by the components of the vacuum system itself or a (test) object 18 which has been placed inside a vacuum environment 11. Throughout the description, the word vacuum will be used for (near) vacuum circumstances as well as for (very) low pressure environments. A pre-concentration device 13 is coupled to the vacuum environment 11. The pre-concentration device 13 comprises a hollow tube 15, which may be made from a material that can withstand low as well as high temperatures. The hollow tube 15 may, e.g., be made of glass. An open end of the hollow tube 15 is coupled to the vacuum environment 11 to receive the gas to be analyzed, which constitutes an entrance opening 20. At the other end the hollow element 15 has a gas outlet to be coupled to a vacuum compatible detector 19, a further (pre-) concentration device 12, or other analysis unit.

The pre-concentration device is further provided with a filler element 14. The filler element is movable (as indicated by the double headed arrow) between a first position (as shown) in the vacuum environment and a second position at least substantially inside the hollow element 15. The first position is used in a collection phase, in which phase the gas to be detected, e.g. out-gassed molecules from the object 18, can freely travel towards the inner wall of the hollow element via the entrance opening 20. Subsequently, in a next phase called the transfer phase, the filler element is moved to the second position. A substantial part of the inner space of the hollow element is now filled. The outer diameter of the filler element is slightly smaller than the inner diameter of the hollow element, leaving open a narrow channel along the inner wall called transfer channel. In the transfer phase the collected gas species are released in the transfer channel, e.g. by heating the hollow element and/or filler element, and transferred via the gas outlet to a detector or a further concentration device.

The filler element 14 may be provided with a closing element 141, e.g. a flange on the filler element, for closing the gas entrance opening in the transfer phase. Alternatively the closing element may be a separate element that is moved to a closed position in front of the entrance opening 20. The closing element may fully close the entrance opening, or a predefined opening may remain. A flow inlet may be provided to admit a transport gas to the starting point of the transfer channel, e.g. via the inlet also used for cooling unit 16 discussed below.

The closing element may reduce, in the transfer phase, the gas entrance opening to a reduced inlet for admitting gas from the vacuum environment for transporting the desorbed gas to the gas outlet.

The inner wall of the hollow tube 15 and/or the outer wall of the filler element may at least partly be covered with a coating of adsorbent particles.

The transport may be made easier by providing a flow inlet 17 for creating a controlled leak to the vacuum environment 11. When adding an amount of a known gas to the vacuum environment 11 via the controlled leak, the transport of gas species, through the device will be promoted. When the amount and/or type of leaked-in gas is known, the measurement results may be corrected for the influence of this gas on the measurement results.

Additionally, the system 11 may comprise a cooling unit 16 for cooling the pre-concentration device 13 or at least the inner wall of the hollow tube 15 and/or the outer wall of the filler element 14 in the collection phase. The pre-concentration device may be provided with one or more ducts for coupling to cooling and/or heating units. Cooling may be done using, e.g., a cooling liquid or a cold gas. For example, liquid nitrogen may be used. The cooling may be performed from the outside of the hollow tube 15 and/or from the inside. Cooling of the inner wall, the filler element and/or any coating thereof, significantly enhances the adsorbing properties of the system and the capacity of the pre-concentration device 13 to, temporarily, store the molecules to be analyzed. Furthermore, the device may have a flow inlet for admitting a purge medium for enabling transporting of the desorbed gas or rinsing of the pre-concentration device.

After collecting the molecular contamination in the pre-concentration device 13 in the collection mode, the adsorbed molecules must be released for analysis in the transfer mode. For best performance, the pre-concentration device 13 should make use of long sampling times. After the collection phase, the pre-concentration device is brought in the transfer position, any cooling is stopped and the pre-concentration device 13 is brought back to ambient temperature, or may be heated by a heating unit to a predefined second temperature well above ambient. The cooling unit 16 may be equipped to also provide said heat, or a separate heating system may be used.

The pre-concentration device 13 is coupled to a second pre-concentration device or vacuum compatible detector for receiving or detecting the molecules that are desorbed from the inner wall of the initial pre-concentration device when the pre-concentration device is heated above a certain temperature.

Figure 2:
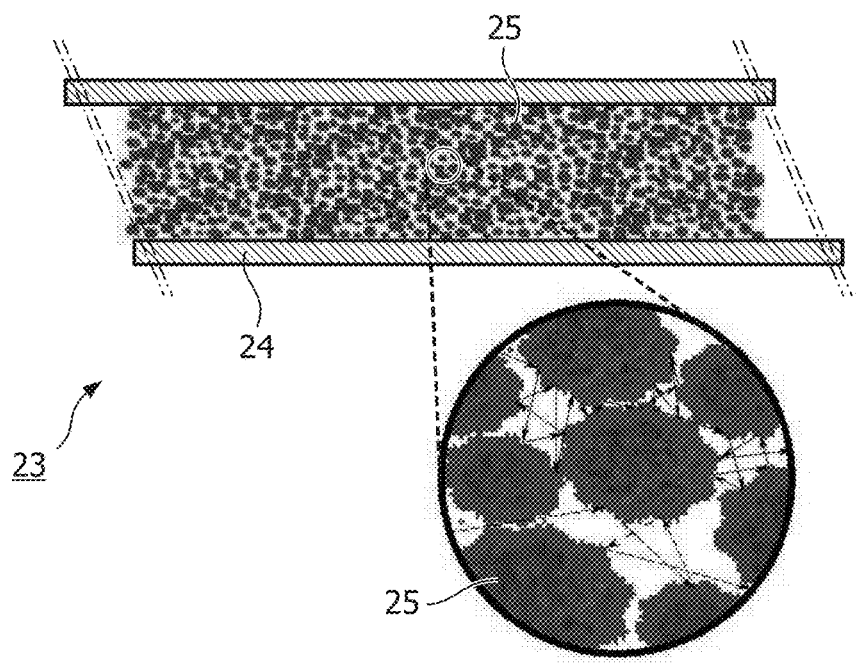
FIG. 2 shows a cross section of a pre-concentration device as used in the prior art.

FIG. 2 shows a cross section of a pre-concentration device 23 as used in the prior art. The pre-concentration device 23 comprises a hollow tube 24 filled with a porous adsorbent 25. The main problem of the use of this prior art pre-concentration device 23 is that the closely packed adsorbent particles 25 cause a drastic decrease of the gas flow in the molecular and transitional phases (vacuum or (very) low pressure).

Figure 3:
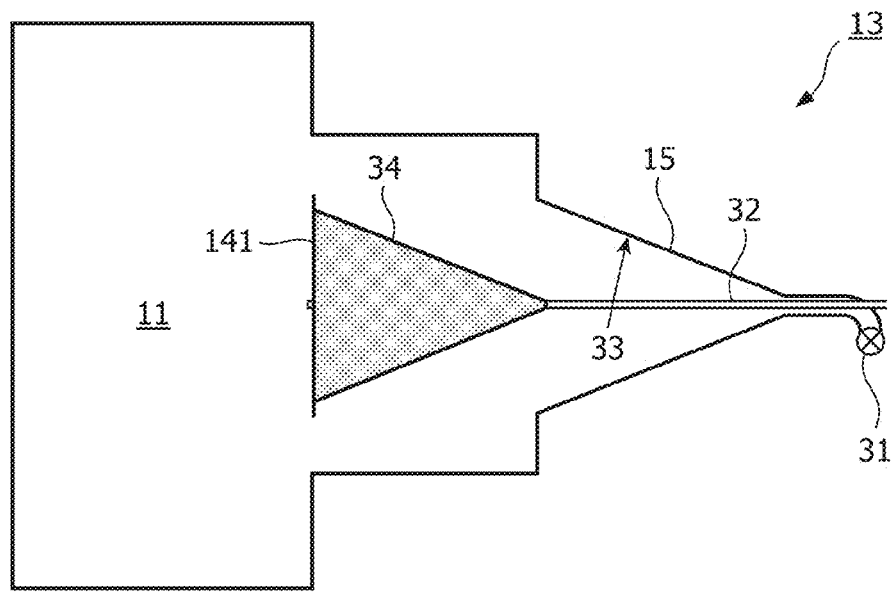
FIG. 3 shows a cross section of a pre-concentration device in the collection phase.
Figure 4:
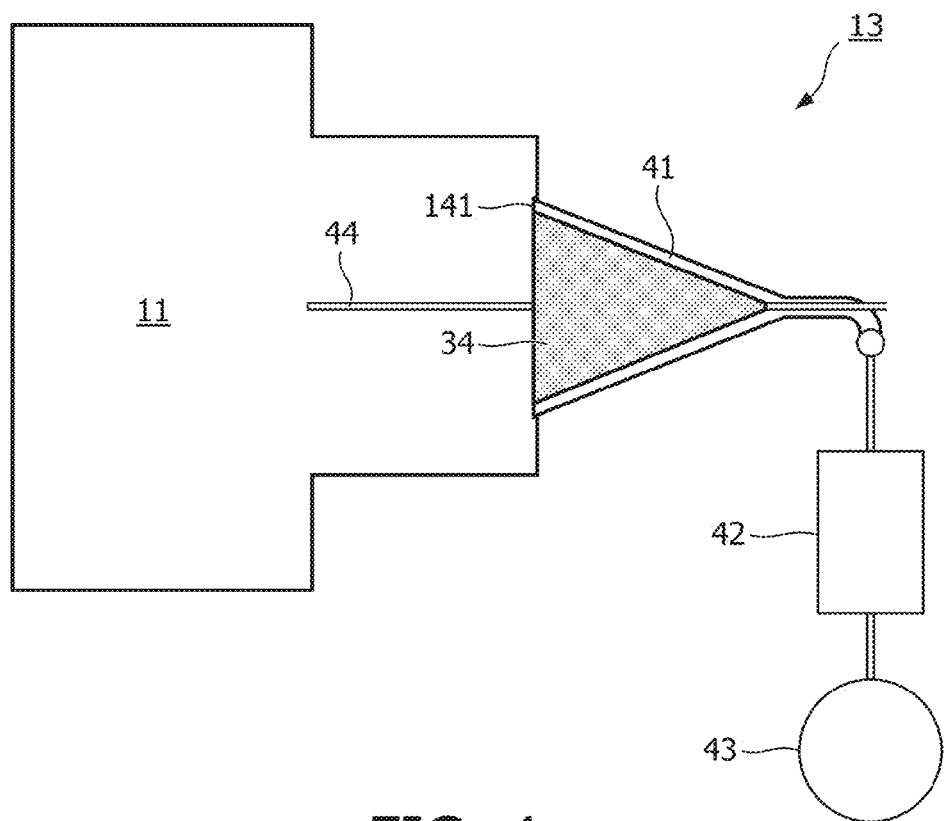
FIG. 4 shows the pre-concentration device of FIG. 3 in the transfer phase coupled to a detector and pump.

FIG. 3 shows a cross section of a pre-concentration device 13 for use in the system 10 in the collection phase. The system has a vacuum environment 11 of which the vacuum possibly contains unwanted molecular contamination. The pre-concentration device is provided with a filler element 14 having a closing rim 141. A guidance rod 32 is provided for moving the filler element from a first position (as shown in FIG. 3) to a second position (as shown in FIG. 4). A gas outlet 31 is provided for coupling the device to a vacuum compatible detector or a further concentration stage. An inner wall 33 of the pre-concentration device is used for adsorbing the gas particles during the collection phase, and desorbing the particles during the transfer phase.

The hollow element 15 has an inner space bounded by an inner wall 33, and the inner space has a conical shape. The filler element 14 has a shape corresponding to the conical shape of the inner space. Due to the corresponding shapes, in the second position, a transfer channel is formed between the filler element 14 and the inner wall 33.

FIG. 4 shows the pre-concentration device of FIG. 3 in the transfer phase coupled to a vacuum compatible detector, a second pre-concentration device and pump. The filler element 14 is movable along guidance element 44. The filler element 14 has been positioned in the second position inside the hollow element, which position leaves open a suited transfer channel 41 to the gas outlet along the inner wall. The gas outlet is coupled to a vacuum compatible detector unit or a second pre-concentration device 42 followed by a pump unit 43. In the transfer phase the pump is activated to pump desorbed molecules via the transfer channel through the vacuum compatible detector or second preconcentration device 42.

Figure 5:
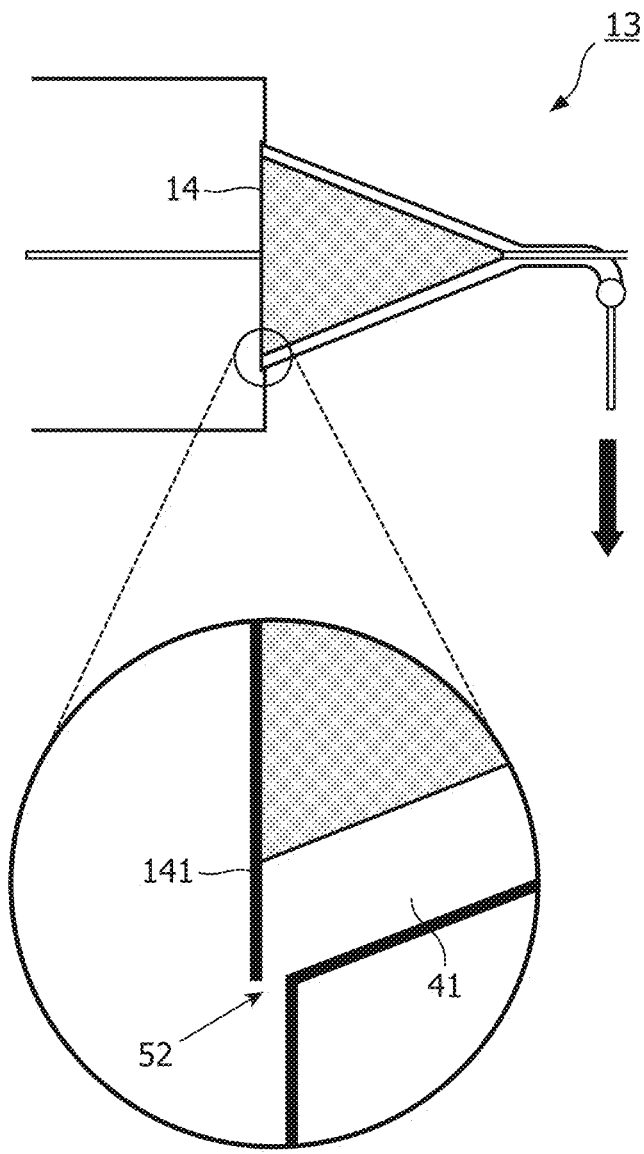
FIG. 5 shows a detail of a closing element.

FIG. 5 shows a detail of a closing element. The pre-concentration device 13 is shown in the transfer phase. A closing element 141, e.g. a flange on the filler element 14, is shown to be near the inner wall while leaving open a reduced inlet 52 for admitting gas from the vacuum environment for transporting desorbed gas to the gas outlet via the transfer channel 41.

The dimensions of the slit depicted as the reduced inlet 52 are critical. The conductivity of the slit must be equal (or slightly smaller) than the conductivity of the detector, analyzer or a further concentration device coupled to the gas outlet. This ensures a maximum flow through the apparatus in the transfer position towards the detector, analyzer or further concentration device and minimizes loss of collected species back into the main vacuum/reduced pressure environment.

It is noted, that control of molecular contamination in advanced semiconductor processing is critical to successful manufacturing. The use of very short wavelengths (Extreme Ultraviolet, EUV; 13.5 nm) increases photo-chemical decomposition and subsequent deposition of contaminants on optical parts. The results are yield loss, shortened tool life and reduced long-term device reliability. Therefore, very strict specifications on the out-gassing of organics are imposed on sub-assemblies and parts used in semiconductor manufacturing equipment.

Qualification of parts to be used in EUV equipment is presently done using RGA (Residual Gas Analysis), a technique based on quadrupole mass spectrometry. This technique has several serious drawbacks making proper qualification with this technique difficult, if not impossible. Drawbacks include, that even if all molecules out-gassed could be led to the mass spectrometer, the limit of detection of RGA is too high to allow measurement of extremely low out-gassing rates. Also, RGA is a vacuum based technique; there is a high probability that components out-gassed will never reach the detector but will be pumped by the vacuum system, thereby leading to an underestimation of the out-gassing rate. Also, RGA uses a mass spectrometric technique and does not allow elemental discrimination necessary to determine out-gassing rates of sulfur, phosphorus, silicon and other hetero-element containing compounds. Moreover, using RGA, it is often difficult or impossible to sample organic contaminants off-line or at customer site. Using RGA it is not possible to identify single (organic) compounds in the complex mixture of organic compounds present in a vacuum system.

The pre-concentration device described above overcomes the problems of previously used cleanliness qualification methods. By using a device with a large entrance opening combined with a large surface area and a small internal volume, extremely low detection limits for organic (and inorganic) contaminants and relatively short sampling times are enabled. The device enables transferring of the organic contaminants collected in the device under vacuum conditions, and only requires a minimal amount of ultra pure gas for the transport of the contaminants to a detector or further a concentration device. This decreases the amount of contamination introduced by the ultra pure gas and lowers the lower limit of detection.

In an embodiment, the pre-concentration device is permanently attached to the low-pressure/vacuum system. In this way no contamination is transferred to the vacuum system (e.g. a EUV system) when attaching the device to the vacuum system. Furthermore, a two-side sealable device may be used which is permanently attached to the low pressure system. This prevents an open contact between the vacuum compatible detector or second pre-concentration device and the reduced pressure/vacuum system. This avoids contamination of the low-pressure/vacuum system by organic or inorganic compounds present in the vacuum compatible detector or second pre-concentration device. Also, using a two-side sealable device enables transfer of the collected organic species to the pre-concentration device at various temperature and pressure conditions up to and exceeding STP (Standard condition for Temperature and Pressure for measurements) when sampling a vacuum/reduced pressure environment containing far more (organic) contamination with respect to the amount of organic contamination in the ultra pure gas used for transport of the collected sample at the chosen conditions.

Using various dimensions of entrance opening, internal volume and internal surface area of the inner wall of the apparatus, chosen with respect to the pressure range and detection limit of interest, can drastically decrease the detection limit of the apparatus.

Various materials may be used for the inner wall, an may be selected for influencing residence times of species of interest, which can enable longer sampling times, and thus decrease detection limits drastically (e.g. metals, ionic liquids, polymers, etc.).

The pre-concentration device is used to collect organic species of which extremely low concentrations are present in a low pressure/vacuum environment and facilitates their transfer to the gas-chromatograph-mass spectrometer (GC-MS) compatible pre-concentration device.

The pre-concentration device provides a large entrance opening and surface area to the hollow element of the pre-concentration device to trap organic species in combination with a small effective internal volume of the hollow element due to the filler element in the transfer phase. The small internal volume is critical for the functionality of the device; after collection of the organic species, their transfer is achieved by desorbing them from the inner wall and flushing them towards a detector or further concentration device where the organic species may be separated from the transport gas used for the transport. To prevent contamination by impurities in the ultra pure gas used to transport the collected organic species, the amount of gas used for transport of the organic species must be extremely low. The volume of the ultra pure gas used for transport of the collected organic species is minimized by two factors; first the small remaining internal volume of the hollow element during desorption and second by desorbing in reduced pressures which causes the gas to expand, resulting in a high volumetric flow using only a small amount of gas.

When pre-concentrating extremely low concentrations of (organic) residual gases in a low pressure/vacuum environment using exiting pre-concentration devices, pre-concentration times can become extremely long. Because residence times of organic species on a (temperature controlled) wall are finite and highly temperature and desorption energy dependent, sampling times are limited ($t_{sampling} < t_{residence}$), which can lead to drastic increase of the lower limit of detection. Because organic species are collected from a low pressure/vacuum environment, the amount of organic contamination entering the sampling interface depends on the surface area of the entrance opening of the device and the pressure at the interface's entrance.

To combine a large entrance opening, a large collection surface and a minimal internal volume, the shape of the inner wall and the filler element may be complementary. In an embodiment, the device consists of two cones. One cone is formed by the inner wall of the hollow element, which may be temperature controlled, and is used to accumulate the organic species. The other cone, which may also be temperature controlled, consists of a slightly smaller, movable solid cone used to minimize the remaining internal volume of the device during desorption in the transfer mode. FIG. 3 shows the pre-concentration device 13 in the "collection" mode, the valve at the gas outlet being closed during collection mode. FIG. 4 shows the pre-concentration device in the "transfer" configuration. Now the valve is open, and collected gas species are transported towards a vacuum compatible detector or second pre-concentration device. The transport is promoted by a pump and/or a transport gas.

During collection of the organic species, the inner cone is in the "first" position outside the hollow element to create a large entrance opening and increase the inner volume of the sampling cone. During collection, organic species and/or other residual gases collide with the inner wall (and/or the outer wall of the filler element) and are retained for a certain amount of time. By choosing a suited wall material combined with a predetermined temperature (e.g. cryogenic temperatures), only residual gases with a certain adsorption energy are retained at the cone's wall for a sufficient amount of time. Because the concentration of the species retained long enough approaches zero at the reduced pressure/vacuum-wall interface, a "pumping" action or transport from the main reduced pressure/vacuum chamber to the hollow element is achieved.

After collection for a sufficient amount of time, which is limited by the residence time of the species collected, the filler cone is moved inside the collection cone, drastically decreasing its internal volume and leaving only a small opening between the main reduced pressure/vacuum chamber and the interface. After the cone is positioned in the "second" position, a valve is opened between the pre-concentration device and a detector or further pre-concentration device, e.g. as described in FIG. 2.

To transport the collected organic species towards the gas outlet in the transfer mode, the inner wall temperature may be increased in order to shorten the residence time of all retained molecules or organic species drastically. The organic species released are transported to the gas outlet by a gas flux at a reduced pressure. The effective pressure in the transfer channel, i.e. the small opening between the inner wall of the device and the filler cone, still enables a sufficient molecular flux from the sampling adsorbing walls trough the gat outlet towards the pump.

The apparatus described in this invention can be applied to the collection and subsequent chemical analysis of contaminants from (process-) gases, components, (sub) assemblies and materials that are used in vacuum or reduced pressure environments requiring extreme cleanliness (e.g., aerospace, EUV lithography and other fields that require qualification for extremely low out-gassing of organics).

Figure 6:
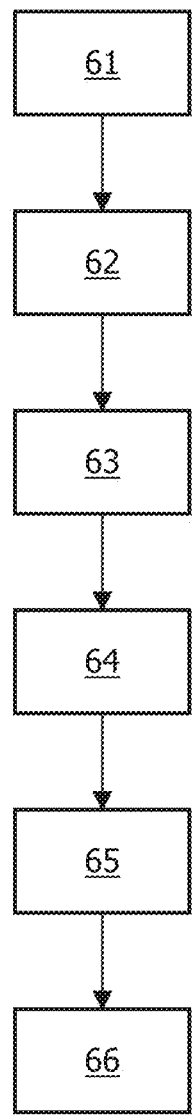
FIG. 6 shows a flow diagram of a method of analyzing gas.

FIG. 6 shows a flow diagram of a method of analyzing gas. The method comprises a step of cooling 61 the pre-concentration device 13 in order to enhance the adsorbing characteristics of the inner wall 33. The filler element 14, which is initially positioned in the vacuum environment outside the hollow element, may also be cooled. Cooling 61 may, e.g., be done using a gaseous or liquid cooling agent which flows through or along the walls of the pre-concentration device 13 and/or the filler element.

When the inner wall is sufficiently cooled, the next step is collecting 62 gas from the vacuum environment 11 on the inner wall of the hollow element 15 of the pre-concentration device 13, and optionally also on the filler element. The molecules are adsorbed during a sampling time by the inner wall and/or the filler element, and optionally on coating particles on the inner wall of the cooled hollow element.

In a next step filling 63 the filler element is moved to a second position inside the hollow element. A closing element may be positioned so as to at least substantially close the gas entrance. The closing element may also be an integral part of the filler element.

After filling (when the total sampling time has passed), the cooling is stopped, because no more molecules have to be adsorbed. Molecules adsorbed earlier stay adsorbed due to the adsorption characteristics of cooled element walls or the adsorbent particles.

In a subsequent heating step 64 the pre-concentration device 13 is heated to release the molecular contamination from the inner wall and/or filler element. Then, in a transfer step 65, the released gas is transferred from the pre-concentration device via a transfer channel to the gas outlet, which may be coupled to a further concentration device or a detector. The directly coupled detector has to be suitable for use in vacuum. The analysis may be performed by an analysis unit operating in vacuum in the system itself. The further concentration device may be removed from the system for further analysis by another system, e.g. washed out under atmospheric pressure. In an analysis step 66, gas chromatography may be used for separation and detection of the released molecular contamination.

For manufacturing the pre-concentration device, in a coating step, adsorbent particles may be applied to the inner wall of the hollow element. Many types of adsorbent particles may be suitable for making a pre-concentration device 13 according to the invention. The type of adsorbent particles used may depend on the type of molecule to be collected by the pre-concentration device 13. Some examples of suitable particles are:

- polymeric materials (solid), e.g. Tenax (diphenylene oxide polymer),
- polymeric materials (liquid), e.g. Silicone polymers, divinylbenzene-styrene copolymers,
- solid materials, e.g. (carbon), alumina (Al2O3), molecular sieves,
- ionic liquids coated on substrate particles, e.g. [1,9-di(3-vinyl-imidazolium) nonane bis(trifluoromethyl) sulfonium imidate
- other materials, including active coal, porous functionalized sol-gel materials.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A method of providing a pre-concentration device for use in detecting molecular contamination in a gas analysis system in a vacuum environment, the method comprising:
    providing a hollow element having a gas entrance opening for receiving gas from a vacuum environment in a collection phase;
    providing an inner wall for adsorbing the gas onto the inner wall in the collection phase, and desorbing the gas from the inner wall in a transfer phase;
    providing a gas outlet for transferring the gas in the transfer phase, and
    providing a filler element that is movable from a first position outside the hollow element in the collection phase to a second position inside the hollow element in the transfer phase which second position leaves open a transfer channel to the gas outlet along the inner wall;
    wherein the hollow element has an inner space bounded by the inner wall, and the inner space has a conical shape, and the filler element has a shape corresponding to the conical shape of the inner space such that, in the second position, the transfer channel is formed between the filler element and the inner wall.

2. A method of operating a pre-concentration device for use in detecting molecular contamination in a gas analysis system in a vacuum environment, the method comprising:
    receiving a gas from a vacuum environment into a hollow element having a gas entrance opening, in a collection phase;
    adsorbing gas on an inner wall in the collection phase;
    desorbing gas from the inner wall in a transfer phase; and
    transferring the gas into a gas outlet of the hollow element, in the transfer phase;
    moving a filler element from a first position outside the hollow element in the collection phase to a second position inside the hollow element in the transfer phase which second position leaves open a transfer channel to the gas outlet along the inner wall.

3. A method of operating a pre-concentrating device in a vacuum environment for use in detecting a molecular contamination in a gas analysis system, the method comprising:
    in a pre-concentration device:
        positioning a filler element in a first position outside a hollow element in a collection phase;
        receiving a gas via a gas entrance opening from a vacuum environment and adsorbing the gas on an inner wall in the collection phase;
        moving the filler element to a second position inside a hollow element in a transfer phase which second position leaves open a transfer channel to the gas outlet along the inner wall; and
        desorbing gas in the transfer phase from the inner wall and transferring the gas to a gas outlet in the transfer phase.

4. The method of claim 1, comprising at least one of the following list of acts:
    cooling the inner wall of the pre-concentration device or the filler element in the collection phase; and
    heating the inner wall of the pre-concentration device or the filler element to release the gas from the inner wall in the transfer phase.

5. The method of claim 1, comprising at least one of the following list of acts:
    gas chromatography analysis of the released gas for determining the molecular contamination;
    mass spectrometry analysis of the released gas for determining the molecular contamination; and
    element selective detection analysis of the released gas for determining the molecular contamination.

6. The method of claim 4, comprising at least one of the following list of acts of:
    gas chromatography analysis of the released gas for determining the molecular contamination;
    mass spectrometry analysis of the released gas for determining the molecular contamination; and
    element selective detection analysis of the released gas for determining the molecular contamination.

7. The method of claim 1, wherein the hollow element has an inner space bounded by the inner wall.

8. The method of claim 7, wherein the inner space has a conical shape.

9. The method of claim 8, wherein the filler element has a shape corresponding to the conical shape of the inner space such that, in the second position, the transfer channel is formed between the filler element and the inner wall.

10. A computer-readable storage-medium that is not a transitory propagating signal or wave, the medium containing control information for controlling a method of operating a pre-concentration device for use in detecting molecular contamination in a gas analysis system in a vacuum environment, the method comprising:
    receiving a gas from a vacuum environment into a hollow element having a gas entrance opening, in a collection phase;
    adsorbing gas on an inner wall in the collection phase;
    desorbing gas from the inner wall in a transfer phase; and
    transferring the gas into a gas outlet of the hollow element, in the transfer phase;
    moving a filler element from a first position outside the hollow element in the collection phase to a second position inside the hollow element in the transfer phase which second position leaves open a transfer channel to the gas outlet along the inner wall.

* * * * *